United States Patent [19]

Bledsoe, Jr. et al.

[11] 4,097,531
[45] Jun. 27, 1978

[54] SUBSTITUTED CYCLOPROPANE PROCESS AND PRODUCT

[75] Inventors: James O. Bledsoe, Jr.; Walter E. Johnson, Jr., both of Jacksonville, Fla.

[73] Assignee: SCM Corporation, New York, N.Y.

[21] Appl. No.: 786,125

[22] Filed: Apr. 11, 1977

Related U.S. Application Data

[63] Continuation-in-part of Ser. No. 692,978, Jun. 4, 1976, abandoned.

[51] Int. Cl.$^2$ .................. C07C 45/00; C07C 49/61
[52] U.S. Cl. .................. 260/586 R; 252/522; 260/586 C; 424/331
[58] Field of Search .................. 260/586 R, 586 C

[56] References Cited

U.S. PATENT DOCUMENTS 3,413,351  11/1968  Eschenmoser et al. ......... 260/586 C

OTHER PUBLICATIONS

Tavel, "Hevl. Chim. Acta", 33, 1266, (1950).

*Primary Examiner*—Norman Morgenstern
*Attorney, Agent, or Firm*—Jerry K. Mueller, Jr.

[57] ABSTRACT

Substituted cyclopropyl ketones can be made by heating unsaturated halo-ketones in the presence of alkaline earth metal carbonate and liquid glycol vehicle.

12 Claims, No Drawings

SUBSTITUTED CYCLOPROPANE PROCESS AND PRODUCT

CROSS-REFERENCE TO RELATED APPLICATIONS

This application is a continuation-in-part of copending application Ser. No. 692,978, filed June 4, 1976, now abandoned.

BACKGROUND OF THE INVENTION

This invention relates to a process for making substituted cyclopropanes, and more particularly vinyl cyclopropyl carbonyl compounds.

While trying to improve on a pseudoionone synthesis reported by Charles Tavel [Helv. Chim. Acta 33, 1266 (1950)] involving the dehydrochlorination of alpha chlorogeranyl acetone (Structure A), new cyclopropyl pseudoionones (products B, C, and D) were obtained.

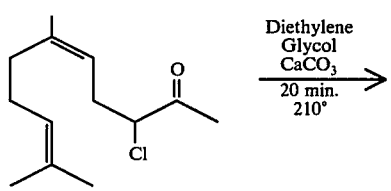

A cis and trans-3-chloro-6,10-dimethyl-5,9-undecadiene-2-one $$\xrightarrow[\text{20 min.}]{\substack{\text{Diethylene}\\ \text{Glycol}\\ \text{CaCO}_3 \\ 210°}}$$

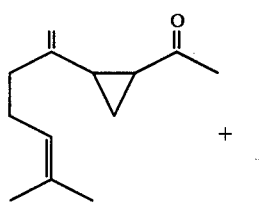

+

B

Methyl 2-[5-methyl-1-methylene-4-hexenyl] cyclopropyl ketone

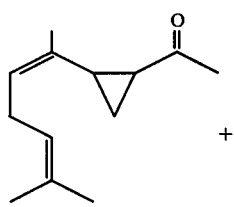

+

C

Methyl 2-[Cis-1,5-dimethyl-1,4-hexadienyl] cyclopropyl ketone

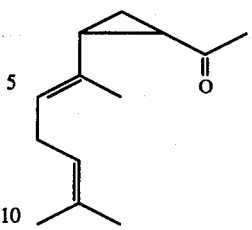

D

Methyl 2-[Trans-1,5-dimethyl-1,4-hexadienyl] cyclopropyl ketone

These compounds, being ionone analogs, can be useful in perfumery as well as intermediates for the synthesis of mimics of juvenile hormones. They have sweet, floral odors. The process is a new and interesting way to make vinyl cyclopropyl ketones.

In a broader sense, the present invention provides a method for making new substituted cyclopropanes represented by the following general formulas:

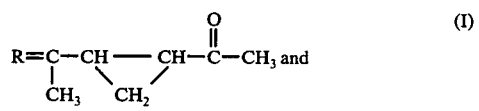
(I)

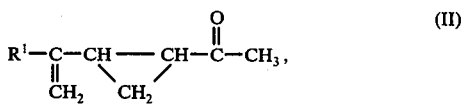
(II)

where R is a monovalent alkyl or alkylene radical, preferably a $C_{1-6}$ alkyl or alkylene radical, and $R^1$ is hydrogen or R. These substituted cyclopropanes (or substituted cyclopropyl ketones) are made by heating at about 100° – 250° C. in the presence of an alkaline earth metal carbonate and liquid glycol vehicle, a compound represented by

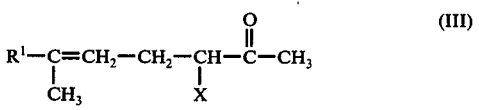
(III)

where X is a halogen, preferably chlorine, until the product cyclopropane is formed. Reaction times vary from about 1 to 20 minutes up to several hours, depending upon reaction temperature and starting material (compound III). Suitable reaction times of 1 – 20 minutes will suffice at elevated temperatures of 200° +, and 4 – 5 hours at about 150° – 160° C., for higher molecular weight starting materials. For lower molecular weight reactants, lower temperatures and longer reaction times often are useful.

Suitable alkaline earth metal carbonates (and bicarbonates) include calcium carbonate, barium carbonate, strontium carbonate, and magnesium carbonate, often provided in pulverant form. About 1 to 8 equivalents of the carbonate per mole of reactant (compound III) is useful. Preferably, the carbonate is calcium carbonate, for economy, in a proportion of about 2.5 equivalents.

The liquid glycol (or polyol) can be an alkylene glycol or polyalkylene glycol, such as diethylene glycol, propylene glycol, ethylene glycol, triethylene glycol and the like. Preferably, diethylene glycol is used for atmospheric operation. of the present invention. The glycol vehicle advantageously is 2 to 20 parts per part of reactant, and preferably about 10 parts for best yields and ease of filtration of solids.

The alpha haloketone reactant most suitably is 3-chlorogeranyl acetone, although other feed stocks such as 3-chloro-6-methyl-5-hepten-2-one and 3-chloro-6-methyl-5-nonen-2-one are suitable. The halogen usually is chlorine, but can also be bromine or iodine.

The examples include the preparation of compounds B, C, and D in the best mode presently known. In this specification all parts are parts by weight, all percentages are weight percentages, and all temperatures are in degrees Centigrade unless otherwise expressly noted.

EXAMPLE 1

In a 250 milliliter three-necked glass flask fitted with a stirrer, thermometer, condenser, addition funnel and a nitrogen gas inlet, a slurry of 40 grams of calcium carbonate (precipitated chalk) and 100 grams of diethylene glycol were stirred and heated to 210° under nitrogen. Thirty grams of alpha chlorogeranyl acetone (Compound A) was added over a five minute period, and, after an additional 45 minutes, the reaction mixture was cooled to 25°, and 300 milliliters of isopropanol was added. Then solids were filtered off. After removal of the isopropanol on a rotary evaporator at reduced pressure, the diethylene glycol was extracted into an aqueous layer by the addition of water, and the whole resulting mass was extracted with ether. The crude product isolated from the ether weighed 27 grams and was distilled to give 12.6 grams (49.9% yield) of a mixture of the three cyclopropyl pseudo-ionones, namely Compounds B, C, and D in a ratio of about 50:22:28, respectively. Fractional distillation on a 2-foot Nester-Faust spinning band column effectively gave pure Compound B, b.p. 62° at 0.2 Torr, but Compounds C and D were obtained in only about 80% purity.

Analysis of Compound B gave: C, 81.02%, H, 10.50%. Calculated for $C_{13}H_{20}O$: C, 81.20%; H, 10.48%.

EXAMPLE 2

A mixture of 45.8 grams (0.2 mole) of chlorogeranyl acetone (Compound A), 22 grams (0.22 gram-atom) of calcium carbonate (precipitated chalk) and 400 grams of diethylene glycol in a 1-liter three-neck flask was heated and stirred under nitrogen at 150° for 4 hours. The reaction mixture was cooled to 90° and filtered. The filtrate was extracted with an equal volume of water, and the whole resulting mass was extracted with ether. The ether extract was dried over magnesium sulfate, and the other removed therefrom on a rotary evaporator. The crude product was strip-distilled at 80°-100°/0.2 Torr. This gave 20.3 grams of product containing (as analyzed by vapor phase chromatography) 96.3% of the three cyclopropyl pseudoionone isomers, Compounds B, C, and D. The theoretical yield of these Compounds was 51%.

When the reaction was perfomed like that of Example 2, except that only 11 grams of calcium carbonate was used, at the end of 2 hours at 150° vapor phase chromatography analysis indicated that a mixture of the desired cyclopropyl pseudoionones and pseudoionones resulted. When this reaction was worked up in the manner of Example 2, 16 grams of a mixture comprising 21% Compound B, 19% Compound C, 14% Compound D, 10% cis-pseudoionone, and 13% trans-pseudoionone resulted. This shows the desirability of using the base fairly liberally.

When a mixture of 22 grams of alpha-chlorogeranyl acetone, 25 milliliters of dimethylformamide, and 10 grams of calcium carbonate (precipitated chalk) was heated to reflux (156° ) the only products detected by vapor phase chromatography analysis after 2½ hours of such heating were cis- and trans- pseudoionones.

Compound B has a carbonyl absorption at 1695 $cm^{-1}$ (5.9 microns) consistent with a cyclopropyl ketone absorption [K. Nakaniski, *Infrared Absorption Spectroscopy*, Holden-Day, Inc. San Francisco, 1962]. And absorption at 888 $cm^{-1}$ (11.26 microns) is characteristic of the terminal methylene. There are also double bond absorptions at 1661 $cm^{-1}$ and 1639 $cm^{-1}$ (6.1 microns). Compound C shows absorptions at 1689 $cm^{-1}$ (5.92 microns) and 1634 $cm^{-1}$ (6.12 microns).

Compound D has absorption bands also at 1689 $cm^{-1}$ (5.92 microns) and 1616 $cm^{-1}$ (6.19 microns).

The nuclear magnetic resonance spectrum of Compound B shows a multiplet for the methylene protons of the cyclopropane ring (C-4) at 1.23 ppm. The vinyl methyls are singlets at 1.64 and 1.71 ppm. The methyl group of the methyl ketone is a singlet at 2.24 ppm. The terminal methylene protons at C-12 are a singlet at 4.75 ppm and the C-9 vinyl proton is a multiplet at 5.13 ppm. The other two cyclopropyl protons overlap with the methylene protons between 1.8–2.2 ppm.

Compound C shows two cyclopropyl hydrogens at 1.26 ppm as a multiplet. There are three vinyl methyl groups at 1.50, 1.64 and 1.72 ppm. The methyl group of the methyl ketone is at 2.28 ppm. The hydrogens at C-8 are now doubly allylic and appear at 2.74 as a triplet.

TABLE I

Nuclear Magnetic Resonance Absorptions of Cyclopropyl Pseudoionones (delta-units)

| Compound | H‚H / C-4Methylens | Vinyl ,C-4Methyls-C—CH$_3$ | O ‖ -C—CH$_3$ | C-12 | C-7 | C-9 | C-8 |
|---|---|---|---|---|---|---|---|
| Compound B | 1.23 (2H)m | 1.64 (3H)s 1.71 (3H)s | 2.24 (3H)s | 4.75 (2H)s | — | 5.13 (1H)m | — |

TABLE I-continued
Nuclear Magnetic Resonance Absorptions of Cyclopropyl Pseudoionones (delta-units)

| Compound | H  H <br> \/ <br> /\ | Vinyl ,C-4Methyls-C—$CH_3$ | O ‖ —$CH_3$ | C-12 | C-7 | C-9 | C-8 |
|---|---|---|---|---|---|---|---|
| Compound C | 1.26 (2H)m | 1.50 (3H)s <br> 1.64 (3H)s <br> 1.72 (3H)s | 2.28 (3H)s | — | 5.38m | 5.18 | 2.74dd |
| Compound D | 1.26 (2H)m | 1.59 (3H)s <br> 1.66 (3H)s <br> 1.73 (3H)s | 2.28 (3H)s | — | 5.31 | 5.18 | 2.82dd |

H = hydrogen atom
m = multiplet
s = singlet
dd = double doublet

Compound D has a very similar nuclear magnetic resonance spectrum to Compound C thus the assignment of the structural difference as being only the C-6,7 cis-trans double bond isomers. Overlap of the C-3 and C-5 cyclopropyl hydrogens in the vinyl methyl region of the nuclear magnetic resonance spectrum makes it difficult to assign stereochemistry of the cyclopropane ring.

The conditions for the reaction in which these products are formed remind one vaguely of the Favorski rearrangement [A. S. Kende, Org. Reactions, 11, 261 (1960)]; but diethylene glycol is not generally used and when carbonates are used they generally employ water as the solvent where alpha-hydroxy ketones are often unwanted byproducts. The instant reaction gives the products in about a 48% theory yield of isolated material. Vapor phase chromatography analysis showed the reaction mixture to be relatively free of byproducts but the greatly reduced area indicated polymer formation or possibly substitution products from the diethylene glycol. The infrared spectrum of the residue from a cyclopropyl pseudoionone distillation showed a hydroxyl band (3367 $cm^{-1}$) and a cyclopropyl ketone band at 1689 $cm^{-1}$. The presence of ether bands indeed indicated the presence of diethylene glycol ethers as well as the absence of double bond absorption bands. Treatment of 25 grams of the residue with 25% phosphoric acid with a continuous steam distillation gave 7.5 grams of a yellow oil that was a mixture of about 20 compounds but showed a major compound (30%) on vapor phase chromatography analysis. Cleavage of the ethers followed by cyclization probably produced a mixture of ionones. Infrared analysis of the mixture showed bands at 1709 $cm^{-1}$, 1664 $cm^{-1}$, and 1613 $cm^{-1}$, but no definite conclusion could be made other than the existence of a saturated ketone along with a mixture of ionones. Vapor phase chromatography-mass spectrometer analyses of the major compound and a few others showed the compounds to be ionone-like but again positive identification was not possible.

The cyclopropyl pseudoionones are stable under the reaction conditions with excess calcium carbonate at 150° but begin to form some new unknown product at 210°. Excess calcium carbonate is desirable since using only an equivalent amount gave a mixture of cyclopropyl pseudoionones and pseudoionones.

Further characterization was done as follows: to a solution of 1 gram of cyclopropyl pseudoionone, Compound D, in 75 milliliters of methanol was added about 0.5 gram of ozone in 6 minutes at −40° from a Welsbach laboratory ozonator. Then 1 gram of dimethyl sulfide in 10 milliliters of methanol was added and the solution allowed to come to room temperature and stir for another 12 hours. The methanol was removed on a rotary evaporator. To the remaining oil was added 50 milliliters of ether and the ethereal solution washed with water to remove the dimethyl sulfoxide. Removal of the ether left a yellow oil, which on vapor phase chromatography analysis showed a major (65%) product, Compound E. Analysis by vapor phase chromatography and mass spectrometer gave the following mass spectral fragments with their respective relative intensities: m/e [m/e is the abbreviation for mass per charged species] 43 (100%), m/e 111 (33%), m/e 83 (20%), m/e 126 (12%), and m/e 55 (12%).

The product was purified by preparative vapor phase chromatography. Its infrared spectrum showed a very strong absorption at 1681 $cm^{-1}$, indicative of a cyclopropyl ketone. The nuclear magnetic resonance spectrum showed: delta 2.34 (6H) S, delta 2.52 (2H) m and delta 1.42 (2H) m, which agrees well with the values of cis-1, 2-diacetyl cyclopropane, Compound E, reported by G. Maier and T. Sayrac, Chem. Ber. 101, 1243 (1968). The cis-2,4-dinitrophenylhydrazone derivative was also prepared and had m.p. 225°. This is also in close agreement with the value of 224° reported for the cis-isomer by Maier and Sayrac, above. Thus, it is believed that the substituents on the cyclopropane ring of Compound D are cis to one another, and it is also very likely that the cyclopropane ring substituents in Compounds B and C are likewise cis.

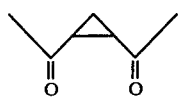

Compound E

EXAMPLES 3 – 5

The procedure in Example 1 was repeated except that the alkaline earth metal carbonate was barium carbonate, strontium carbonate, and magnesium carbonate in three different runs of such procedure. Substantially identical results were obtained in each of the three runs as are reported in Example 1.

EXAMPLE 6

The procedure of Example 1 was repeated except that the liquid glycol vehicle was propylene glycol. Again, substantially identified results were obtained here as are reported in Example 1.

EXAMPLE 7

The reactant haloketone (Compound III) was prepared by reacting 50 grams of 3-methyl-1-hexen-3-ol and 71.8 grams of ethyl 2-chloroacetoacetate at 150° C. for 20 hours in the presence of 1 gram of sodium acetate catalyst with removal of ethanol. The reaction mixture was distilled for recovery of 12 grams of 3-chloro-6-methyl-5-nonen-2-one (boiling point of 72° C. at 1 Torr). Infrared and nuclear magnetic resonance spectra were consistent with the following proposed structure for the product:

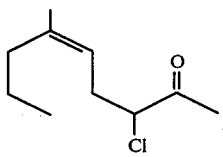

cis and trans-3-chloro-6-methyl-5-nonen-2-one        IV

A mixture of 7.2 grams of compound IV, 100 grams of diethylene glycol, and 12 grams of powdered calcium carbonate was heated at 120° C. for 9 hours under stirring. The reaction mixture then was cooled to 90° C. and the solids filtered off. The filtrate was diluted with water and the resulting mass extracted with ether. The ether layer was dried and the ether removed to yield 7 grams of oil. The oil was distilled and 2.6 grams of product cyclopropane recovered (boiling point of 70°–72° C. at 1.5 Torr). The product cyclopropane consisted of a 39:25:36 mixture of three cyclopropanes whose structures are as follows:

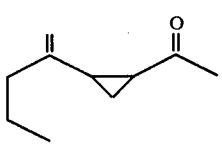

methyl 2-[1-methylenebutyl] cyclopropyl ketone        V

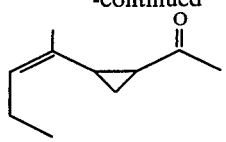

methyl 2-[cis-1-methyl-1-butenyl] cyclopropyl ketone        VI

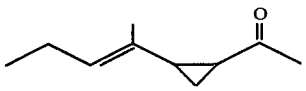

methyl 2-[trans-1-methyl-1-butenyl] cyclopropyl ketone        VII

Infrared analysis of the mixture showed bonds at 1695 cm$^{-1}$ (cyclopropyl ketone), at 1639 cm$^{-1}$ (carbon-carbon double bond), and at 888 cm$^{-1}$ (terminal methylene group). The nuclear magnetic resonance spectrum of the mixture confirmed the presence of the following types of hydrogen atoms: primary methyl group, cyclopropyl, vinyl, methyl, methyl ketone, terminal methyl, and trisubstituted double bond.

We claim:

1. A substituted cyclopropane selected from the group represented by the following general structures:

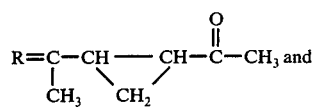

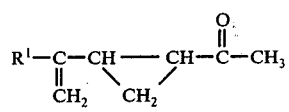

where R is a monovalent alkyl or alkylene radical, and R$^1$ is hydrogen or R.

2. The substituted cyclopropane of claim 1 wherein R is a monovalent C$_{1-6}$ alkyl or alkylene radical.

3. The substituted cyclopropane of claim 1 selected from methyl 2-[5-methyl-1-methylene-4-hexenyl] cyclopropyl ketone, methyl 2-[cis-1,5-dimethyl-1, 4-hexadienyl] cyclopropyl ketone, and methyl 2-[trans-1, 5-dimethyl-1, 4-hexadoenyl] cyclopropyl ketone.

4. The substituted cyclopropane of claim 1 selected from methyl 2-[1-methylenebutyl] cyclopropyl ketone, methyl 2-[cis-1-methyl-1-butenyl] cyclopropyl ketone, and methyl 2-[trans-1-methyl-1-butenyl] cyclopropyl ketone.

5. The process for making substituted cyclopropane represented by the following general structures:

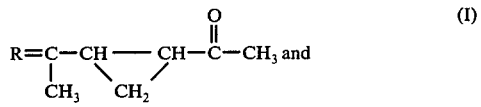   (I)

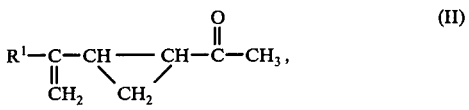   (II)

where R is a monovalent alkyl or alkenyl radical, and R$^1$ is hydrogen or R, which comprises:

heating at about 100° to 250° C. in the presence of an alkaline earth metal carbonate and liquid glycol vehicle, a compound represented by

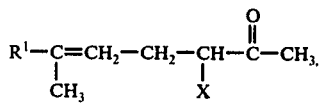

(III)

where X is a halogen atom, until said substituted cyclopropane is formed.

6. The process of claim 5 wherein R is a monovalent $C_{1-6}$ alkyl or alkylene radical.

7. The process of claim 5 wherein said alkaline earth metal carbonate is calcium carbonate.

8. The process of claim 5 wherein said liquid glycol vehicle is an alkylene glycol.

9. The process of claim 8 wherein said alkylene glycol is diethylene glycol.

10. The process of claim 5 wherein said carbonate is calcium carbonate and said vehicle is diethylene glycol.

11. The process of claim 5 wherein said substituted cyclopropane is selected from methyl 2-[5-methyl-1-methylene-4-hexenyl] cyclopropyl ketone, methyl 2-[cis-1, 5-dimethyl-1, 4-hexadienyl] cyclopropyl ketone, and methyl 2-[trans-1, 5-dimethyl-1, 4-hexadienyl] cyclopropyl ketone, and said Compound (III) is cis-, and trans-3-chloro-6, 10-dimethyl-5, 9-undecadiene-2-one.

12. The process of claim 5 wherein said substituted cyclopropane is selected from methyl 2-[1-methylenebutyl] cyclopropyl ketone, methyl 2-[cis-1-methyl-1-butenyl] cyclopropyl ketone, and methyl 2-[trans-1-methyl-1-butenyl] cyclopropyl ketone and said Compound (III) is cis-, and trans-3-chloro-6-methyl-5-nonene-2-one.

* * * * *